United States Patent
Verboom et al.

(10) Patent No.: US 8,277,789 B2
(45) Date of Patent: *Oct. 2, 2012

(54) METHOD FOR INHIBITING FADING AND ENHANCING COLOR INTENSITY OF COLOR-TREATED HAIR

(75) Inventors: Gilles Verboom, St. Charles, IL (US); Kari Bauer, Oak Park, IL (US); Perry Romanowski, Chicago, IL (US)

(73) Assignee: Conopco, Inc., Englewood Cliffs, NJ (US)

( * ) Notice: Subject to any disclaimer, the term of this patent is extended or adjusted under 35 U.S.C. 154(b) by 293 days.

This patent is subject to a terminal disclaimer.

(21) Appl. No.: 12/303,689

(22) PCT Filed: Jun. 5, 2007

(86) PCT No.: PCT/US2007/070417
§ 371 (c)(1),
(2), (4) Date: Nov. 12, 2010

(87) PCT Pub. No.: WO2007/146672
PCT Pub. Date: Dec. 21, 2007

(65) Prior Publication Data
US 2011/0044924 A1      Feb. 24, 2011

Related U.S. Application Data

(60) Provisional application No. 60/811,282, filed on Jun. 6, 2006.

(51) Int. Cl.
*A61Q 5/00*      (2006.01)

(52) U.S. Cl. .................................. 424/70.28; 424/70.1
(58) Field of Classification Search .................. None
See application file for complete search history.

(56) References Cited

U.S. PATENT DOCUMENTS

| | | | | |
|---|---|---|---|---|
| 5,389,364 | A | * | 2/1995 | Cifuentes et al. ........ 424/70.122 |
| 6,143,286 | A |   | 11/2000 | Bhambhani et al. |
| 6,294,159 | B1 | * | 9/2001 | Reich et al. ................ 424/70.12 |
| 6,709,468 | B2 |   | 3/2004 | Patel et al. |
| 6,887,400 | B1 |   | 5/2005 | Wei et al. |
| 6,936,735 | B2 |   | 8/2005 | Chaudhuri |
| 2004/0244126 | A1 |   | 12/2004 | Vena et al. |

FOREIGN PATENT DOCUMENTS

| | | |
|---|---|---|
| WO | WO 99/55295 A1 | 11/1999 |
| WO | WO 00/07550 A1 | 2/2000 |
| WO | WO 03/074016 A1 | 9/2003 |
| WO | WO 2004/020398 A1 | 3/2004 |

* cited by examiner

*Primary Examiner* — Jyothsna Venkat
(74) *Attorney, Agent, or Firm* — Ronald A. Koatz

(57) ABSTRACT

The invention provides a method for inhibiting color fading in color-treated keratinous fibers, which method includes treating the keratinous fibers with a color-fade inhibiting-effective effective amount of a monoalkyl quaternary ammonium salt. The invention also provides a method for enhancing the intensity of color in color-treated keratinous fibers, which method includes treating the keratinous fibers with a color intensity enhancing effective amount of an alkyl a quaternary ammonium salt. Additionally provided are products for inhibiting the fading of color and increasing the intensity of color in color-treated keratinous fibers.

12 Claims, No Drawings

METHOD FOR INHIBITING FADING AND ENHANCING COLOR INTENSITY OF COLOR-TREATED HAIR

BACKGROUND OF THE INVENTION

It is common practice to alter or enhance the natural color of hair by coloring the hair, e.g., by applying hair dyes. However, color-treated hair is subject to fading due to exposure to the elements (e.g., sunlight and air), shampooing, blow-drying, heating, combing and styling. Consequently, efforts have been undertaken to develop products and methods for protecting or inhibiting color fading of color-treated hair.

Products and methods for protecting color-treated hair have been described, for example, in WO 02/30373 (to Henkel), which describes the use of short-chain aldehydes and formaldehyde releasing compounds to improve color stability in dyed hair. In addition, WO 99/55295 (to Proctor &Gamble Co.) describes the use of various conditioning agents for preventing or reducing color fade in dyed hair.

There is a need for improved methods and products for preventing the fading of color in color-treated hair. The present invention provides such methods and products.

BRIEF SUMMARY OF THE INVENTION

The present invention provides methods and products for inhibiting the fading of color in color-treated keratinous fibers (e.g., hair) and for increasing the color intensity of color-treated keratinous fibers (e.g., hair). In one embodiment, the present invention provides a method for inhibiting color fading in color-treated keratinous fibers, which method preferably includes contacting keratinous fibers (e.g., color-treated keratinous fibers, e.g., color-treated hair) with a composition comprising a carrier and a monoalkyl quaternary ammonium salt in an amount effective to inhibit the fading of color in the keratinous fibers when color treated. Preferably, the keratinous fibers (e.g., hair or color-treated hair) are contacted with the composition for a period of time effective for the monoalkyl quaternary ammonium salt to inhibit (e.g., prevent or reduce the rate of) fading of color in the keratinous fiber(s) when color-treated prior to or following application of the composition.

In another embodiment, the present invention provides a product (e.g., a hair care product), which preferably includes a container, a composition contained within the container, and instructions for applying the composition to inhibit color fading of color-treated hair, wherein the composition comprises a carrier and a color fading inhibiting-effective amount of a monoalkyl quaternary ammonium salt.

In yet another embodiment, the present invention provides a method for inhibiting color fading in color-treated keratinous fibers, which method preferably includes contacting the keratinous fibers, e.g., by pre-treating keratinous fibers prior to color treatment, with a composition comprising a carrier and a monoalkyl quaternary ammonium salt in an amount effective to inhibit the fading of color in the keratinous fibers, and color-treating the keratinous fibers.

The composition preferably contains from about 0.1 wt % to about 15 wt % of the monoalkyl quaternary ammonium salt based on the weight of the composition. The monoalkyl quaternary ammonium salt can include one monoalkyl quaternary ammonium salt or a combination of one or more monoalkyl quaternary ammonium salts. The composition applied in accordance with the method of the present invention can further include, e.g., from about 0.05 wt % to about 10 wt % of a surfactant, and water.

The present invention additionally provides a method for enhancing the intensity of color in color-treated keratinous fibers, which method preferably includes contacting keratinous fibers with a composition comprising a carrier and an alkyl quaternary ammonium salt in an amount effective amount to increase the intensity of color in the keratinous fibers, and color-treating the keratinous fibers, wherein color intensity achieved by color-treating the keratinous fibers following contact with the composition is greater than the color intensity achieved by color-treating the keratinous fibers untreated with the composition. Preferably, the method includes pre-treating hair with a composition containing a carrier and, e.g., from about 0.1 wt % to about 15 wt % of the alkyl quaternary ammonium salt (or a suitable combination of alkyl quaternary ammonium salts), and thereafter color-treating, wherein the color intensity following color treatment is greater than that which is otherwise achieved by color treating the hair untreated with the composition.

The present invention further provides products for inhibiting color fading and increasing the color intensity of color-treated hair utilizing the compositions applied in accordance with the present invention.

DETAILED DESCRIPTION OF THE INVENTION

The present invention provides methods for inhibiting fading in color-treated keratinous fibers (e.g., hair) and for achieving greater, e.g., enhancing, color intensity in color-treated keratinous fibers (e.g., hair), which methods include contacting keratinous fibers (e.g., hair or color-treated hair) with an effective amount of a composition that contains an effective amount of one or more suitable quaternary ammonium salts. It is believed that the quaternary ammonium salts applied in accordance with the present invention, particularly low molecular weight quaternary ammonium salts, can penetrate into keratinous fibers, e.g., hair. See, e.g., Reutsch, *J. Cosmet. Sci.*, 56, 323-330 (2005) and Keis, *J. Cosmet. Sci.*, 56, 283-295 (2005), which teach that certain oils and low molecular weight quaternary ammonium salts, such as cetyl trimethyl ammonium bromide, are capable of penetrating the hair fiber to the cuticle thereby conditioning and extending the fatigue life of tested strands. Without wishing to be bound by any particular theory, it is believed the quaternary ammonium salt(s) that penetrate into the hair shaft can create stearic hindrance within the hair shaft, which prevents color-treating reagents, e.g., hair dye, from leaching out or from being washed out of the hair shaft, allowing a greater amount of dye to be retained in the hair shaft, resulting in longer lasting color. It has also been found that the intensity of color achieved by color treatment can be enhanced when the hair is color treated following application of the quaternary ammonium salt in accordance with the present invention.

In one embodiment, the present invention provides a method for inhibiting color fading in color-treated keratinous fibers, which method preferably includes contacting color-treated keratinous fibers, e.g., color-treated hair, with a composition comprising a carrier and a color fading inhibiting-effective amount of a monoalkyl quaternary ammonium salt. Preferably, the color-treated keratinous fibers (e.g., color-treated hair) are contacted with the composition for a period of time effective for the monoalkyl quaternary ammonium salt to inhibit (e.g., prevent or reduce the rate of) fading of the color in the color-treated keratinous fibers relative to the fading of color in the color-treated keratinous fibers when untreated with the composition. The keratinous fibers can include hair such as, e.g., mammalian hair (e.g., human hair). Preferably, the keratinous fibers include human hair.

The color fade-inhibiting monoalkyl quaternary ammonium salts applied to the keratinous fibers in accordance with the method of the present invention preferably include at least one compound of formula I:

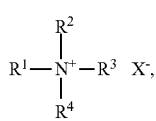

wherein $R^1$ is preferably a $C_6$-$C_{18}$ alkyl, $R^2$ and $R^3$ are the same or different and each is preferably a methyl or a hydrogen, $R^4$ is preferably a hydrogen, a methyl or an aralkyl comprising 7 carbon atoms, and X is salt forming anion. Preferably, $R^1$ is a C-8 to C-12 alkyl. In one embodiment, the monoalkyl quaternary ammonium salt is a compound of formula (I), wherein $R^1$ is a $C_{12}$ alkyl.

Exemplary salt forming anions (X) include, but are not limited to, halogen, acetate, citrate, lactate, glycolate, phosphate, nitrate, sulfonate, sulfate, alkylsulfate, alkylaryl sulfate, sulfonate radicals, and combinations thereof. Preferably, X is a chloride, a bromide or a methoxysulfonate.

Exemplary monoalkyl quaternary ammonium salts, which can be used in accordance with the color fade inhibiting method of the present invention, include, but are not limited to, lauryltrimonium chloride, cocotrimonium chloride, cetrimonium chloride, oleyl alkonium chloride, and combinations thereof.

Preferably, the composition applied in accordance with the color fade inhibiting method contains from about 0.1 wt % to about 15 wt % of the monoalkyl quaternary ammonium salt, which can include a combination of one or more monoalkyl quaternary ammonium salts, based on the weight of the composition. More preferably, the composition includes from about 0.25 wt % to about 10 wt % of the monoalkyl quaternary ammonium salt.

The pH of the composition preferably is from about 3.5 to about 10. More preferably, the pH of the composition is from about 5.0 to about 9.0, e.g., from about 6.0 to about 8.0.

The composition applied in accordance with the color fade inhibiting method of the present invention also can include one or more surfactants, e.g., one or more water-soluble or hydrophilic surfactants. The surfactant can include, for example, water-soluble amodimethicones, water-soluble nonionic surfactants, water-soluble ionic surfactants, water-soluble amphoteric surfactants, and the like, and combinations thereof. Exemplary surfactants include, without limitation, trideceth-9/12 PG amodimethicone (for example, Clariant Silcare Silicone SEA), diquaternary polydimethyl-siloxane (for example, Quaternium-80 or Quat 80), methoxy PEG/PPG-7/3 aminopropyl dimethicone (for example, Degussa ABIL SOFT AF-100), bisamino PEG/PPG-41/3 aminoethyl PG-propyl dimethicone (for example, GE Silsoft A-843), and the like, and combinations thereof. The surfactant can be present in the composition, e.g., in an amount of from about 0.05 wt % to about 10 wt %, e.g., in an amount of from about 0.1 wt % to about 2.0 wt %.

The composition can further include, e.g., one or more emulsifiers, thickeners, preservatives, UV protectants, antioxidants, pH adjusting agents, botanical extracts, emollients, fragrances, gelling agents, moisturizing and conditioning agents, and the like, and combinations thereof, which are commonly used in hair care products.

Suitable emulsifiers can include emulsifiers that are commonly used in hair care products and can include compounds such as, for example, isoceteth-20, dicetyl phosphate, ceteth-10-phosphate, sodium stearate, stearic acid, cetearyl alcohol, stearamidopropyldimethylamine, behentrimonium methosulfate, sodium methyl cocoyl taurate, cetearyl glucoside, sodium methyl oleoyl taurate, sodium lauryl sulfate, and the like, and combinations thereof.

Suitable thickeners can include, for example, xanthan gum, guar gum, hyoroxyethyl cellulose, methyl cellulose, hydroxyethylcellulose, starch and starch derivatives, viscosity modifiers (e.g., methanolamides of long chain fatty acids such as, e.g., cocomonoethanol amide) also fatty alcohols, acrylates and acrylates copolymers, crystalline suspending agents, pearlescent aids (e.g., ethylene glycol distearate), and the like, and combinations thereof.

Suitable preservatives can include, for example, benzyl alcohol, methyl paraben, propyl paraben, imidazolidinyl urea, polyvinyl alcohol, ethyl alcohol, DMDM hydantoin, methylchloroisothiazolinone, methylisothiazolinone, and the like, and combinations thereof.

Suitable UV protectants (which include agents that protect against UVA and UBV) can include, for example, 2-ethylhexyl p-methoxycinnamate, 2-ethylhexyl N,Ndimethyl-p-aminobenzoate, p-aminobenzoic acid, 2-phenylbenzimidazole-5sulfonic acid, octocrylene, oxybenzone, homomethyl salicylate, octyl salicylate, 4,4'-methoxy-1-butyldibenzoyl methane, 4-isopropyl dibenzoylmethane, 3-benzylidene camphor, 3-(4-methylbenzylidene) camphor, titanium dioxide, zinc oxide, silica, iron oxide, Parsol MCX, Eusolex 6300, Octocrylene, Parsol 1789, 4-N,N-(2-ethylhexyl)methylaminobenzoic acid ester of 2,4-dihydroxybenzophenone, 4-N,N-(2-ethylhexyl)methylaminobenzoic acid ester with 4-hydroxydibenzoylmethane, 4-N,N-(2-ethylhexyl) methylaminobenzoic acid ester of 2-hydroxy-4-(2-hydroxyethoxy)benzophenone, 4-N,N-(2-ethylhexyl) methylaminobenzoic acid ester of 4-(2-hydroxyethoxy) dibenzoylmethane, sodium benzotriazolyl butyl phenol sulfonate and the like, and combinations thereof.

Suitable antioxidants can include, for example, tocopheryl acetate, butylated hydroxy toluene, polyphenols and extracts known in the art for their anti oxidant properties (e.g. green tea, grape seed extracts and others) and the like, and combinations thereof.

Examples of pH adjusting agents that may be incorporated into the composition can include, for example, citric acid, sodium citrate, succinic acid, phosphoric acid, sodium hydroxide, sodium carbonate; and salts, in general, such as potassium acetate and sodium chloride.

Suitable carriers can include, for example, water, alcohols, glycols (e.g. propylene glycol). A preferred carrier is water.

The composition also may contain DMDM hydantoin, diazolidinyl urea, or a combination thereof. DMDM hydantoin can be present, for example, in an amount of from about 0.1 wt % to about 5.0 wt %, e.g., about 1.0 wt %. In compositions containing diazolidinyl urea, the diazolidinyl urea can preferably present, for example, in an amount of from about 0.1 wt % to about 1.0 wt %, e.g., about 0.4 wt %.

In accordance with the present invention, the keratinous fibers may be contacted with the composition before being color-treated, following color treatment, or both. In either embodiment, the keratinous fibers may be contacted with the composition for a period of time ranging from about 0.5 minutes to about 30 minutes. Preferably, the keratinous fibers are contacted with the composition for a period of time between about 1 minute and about 10 minutes, and more preferably from about 1 minute to about 5 minutes.

Preferably, the method of the present invention includes contacting hair with a composition containing from about 0.1 wt % to about 15 wt % of a monoalkyl quaternary ammonium salt, about 0.05 wt % to about 10 wt % of a surfactant, and a carrier, which is preferably water. The hair is preferably contacted for a period of time effective for the composition to inhibit fading of color in the hair when the hair is color-treated prior to application of the composition.

In another embodiment, the present invention provides a method for inhibiting the fading of color in color-treated keratinous fibers, which method includes contacting the keratinous fibers (e.g., by pre-treating the keratinous fibers prior to color treatment) with a composition containing a monoalkyl quaternary ammonium salt in an amount effective to inhibit the fading of color in the keratinous fibers when the hair is color-treated following application of the composition, and thereafter color-treating the keratinous fibers.

The present invention also provides a product for treating keratinous fibers, which is preferably hair care product, which product includes a container, a composition contained within the container and instructions for applying the composition to keratinous fibers (e.g., hair) inhibit color fading in color-treated keratinous fibers, wherein the composition preferably includes a carrier and a color fading inhibiting-effective amount of a monoalkyl quaternary ammonium salt.

The present invention further provides a method for enhancing the intensity of color in color-treated keratinous fibers, which method includes contacting keratinous fibers with a composition comprising a carrier and an alkyl quaternary ammonium salt in an amount effective to increase the intensity of color of the keratinous fibers following color treatment, and color-treating the keratinous fibers. The intensity of color achieved by color-treating the keratinous fibers treated in accordance with the method of the present invention is greater than the intensity of color achieved when the keratinous fibers are untreated with the alkyl quaternary ammonium salt. Preferably, the quaternary ammonium salt used for enhancing color intensity in accordance with the method of the present invention includes at least one compound of formula II:

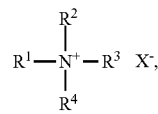

(II)

wherein $R^1$ is preferably a $C_6$-$C_{18}$ allyl, $R^2$ is preferably a $C_6$-$C_{18}$ alkyl, a methyl or a hydrogen, $R^3$ is preferably a methyl or a hydrogen, $R^4$ is preferably an aralkyl comprising 7 carbon atoms, a methyl or a hydrogen, and X is a salt forming anion such as, for example, a halogen, acetate, citrate, lactate, glycolate, phosphate, nitrate, sulfonate, sulfate, alkylsulfate, alkylaryl sulfate, sulfonate radicals, and combinations thereof (preferably chloride, bromide or methoxysulfonate). In one embodiment, $R^1$ and $R^2$ are the same or different and each is a $C_6$-$C_{18}$ alkyl. In another embodiment, $R^1$ is a $C_6$-$C_{18}$ alkyl, $R^2$ and $R^3$ are the same or different and each is a hydrogen or a methyl, and $R^4$ is a hydrogen, a methyl, or an aralkyl comprising 7 carbon atoms.

Examples of quaternary ammonium salts suitable for enhancing color intensity in accordance with the method of the present invention include, but are not limited to, laurylt-rimonium chloride (for example, ARQUAD 12-37W), cocotrimonium chloride (for example ARQUAD C-33W), cetrimonium chloride (for example Varisoft 300), oleyl alkonium chloride, dilauryldimethylammonium chloride, dicocodimethylammonium chloride (for example, ARQUAD 2C-70PG), dicetyldimethylammonium chloride, dioleyldimethylammonium chloride, and the like, and combinations thereof. Preferred quaternary ammonium salts, which can be used for enhancing color intensity in accordance with the method of the present invention, include, e.g., lauryltrimonium chloride (for example, ARQUAD 12-37W), cocotrimonium chloride, cetrimonium chloride, oleyl alkonium chloride, and combinations thereof.

The color intensity enhancing amount of the alkyl quaternary ammonium salt (which can include one or more alkyl quaternary ammonium salts) is preferably from about 0.1 wt % to about 15 wt % of the quaternary ammonium salt(s), e.g., from about 0.25 wt % to about 10 wt % of the quaternary ammonium salt(s). Such compositions can further include, e.g., a surfactant and other additives as described herein.

The method of increasing color intensity in accordance with the method of the present invention preferably includes contacting the keratinous fibers with the composition, which contains a color intensity-enhancing effective amount of the quaternary ammonium salt, for from about 0.1 minutes to about 30 minutes, and more for from about 0.5 minutes to about 10 minutes, and thereafter color treating the hair. In a preferred embodiment, the method of increasing color intensity in accordance with the method of the present invention includes contacting hair with a composition containing from about 0.1 wt % to about 15 wt % of one or more alkyl quaternary ammonium salts, from about 0.05 wt % to about 10 wt % of a surfactant, and a carrier, which is preferably water, and thereafter color treating the hair.

The present invention additionally provides a product for treating keratinous fibers, e.g., a hair care product, which product includes a container, a composition contained within the container, and instructions for applying the composition to keratinous fibers, e.g., hair, and thereafter color treating the keratinous fibers, wherein the composition includes an alkyl quaternary ammonium salt in an amount effective to increase the intensity of color of the keratinous fibers, e.g., hair, when color treated following application of the composition.

The following examples further illustrate the present invention but, of course, should not be construed as in any way limiting its scope.

EXAMPLE 1

This example demonstrates the application of monoalkyl quaternary ammonium salts to afford color fade protection to dyed tresses.

Small tresses were dyed with either CLAIROL Ultress Burgandy (tress nos. 1-28) or GARNIER 100% Color #660 Intense Auburn (tress nos. 29-33). The dyed tresses were then dipped for 10 minutes into the DI water solutions described in Tables 1-4. The tresses were then blow dried and allowed to stand at room temperature. The tresses were then soaked in DI water overnight and then blown dry the following day. A visual evaluation against a control consisting of a dyed tress soaked in water overnight with no prior dipping was carried out. The results of the experiment are shown in Tables 1-4.

TABLE 1

| INGREDIENT | Comparative Samples | | | | Invention |
|---|---|---|---|---|---|
|  | 2 | 3 | 4 | 5 | 7 |
| Hercules Aquacat liquid guar | 1% | 0.8% | 2% |  |  |
| Clariant SilCare Silicone SEA | 2% | 1% | 1% | 1% | 1% |
| Polyquaternium-10 |  | 0.6% | 0.2% |  |  |
| Cocotrimonium Chloride (34%) |  |  |  |  | 2% |
| Visual Evaluation of Color Fade Protection | Similar to water soak. | Similar to water soak. | Similar to water soak. | Similar to water soak. | Retained noticeably more reddish color than water soak |
| Overall Grade | Poor | Poor | Poor | Poor | Good |

TABLE 2

| INGREDIENT | 7' | 11 | 16 | 14 (comparative) | 15 | 12 | 17 | 20a (comparative) |
|---|---|---|---|---|---|---|---|---|
| Clariant SilCare Silicone SEA | 1% | 1% | 1% | 1% |  |  |  |  |
| Cocotrimonium Chloride (34%) | 2% |  |  |  | 2% | 2% | 2% |  |
| Cetrimonium Chloride (30%) |  | 2% |  |  |  |  |  |  |
| Olealkonium Chloride (30%) |  |  | 2% |  |  |  |  |  |
| Quateraium-80 (50%) |  |  |  | 2% | 1% |  |  |  |
| GE Silsoft A-843 (25%) |  |  |  |  |  |  | 1% | 1% |
| Degussa Abilsoft AF100 |  |  |  |  |  |  | 1% |  |
| Visual Evaluation of Color Fade Protection | Similar to previous 7. | Less red, more brown color than 7. | Similar to 11; maybe slightly more red and less brown. | Color similar to 11, but lighter. Not much darker than water soak. | Similar to 7'. | Similar to 7'. Nearly as good as 7a. | Similar to 7. Slightly less color than 7'. | Only slightly more color retained than water soak. |
| Overall Grade | Good | Fair | Fair | Poor | Good | Good | Fair-Good | Poor |

TABLE 3

| INGREDIENT | 24a | 24b | 24c | 24d | 24e |
|---|---|---|---|---|---|
| GE Silsoft A-843 (25%) | 1% | 1% | 1% | 1% | 1% |
| Cocotrimonium Chloride (34%) | 2% | 2% | 2% | 2% | 2% |
| Dipping Time | 2 min | 4 min | 6 min | 8 min | 10 min |
| Visual Evaluation of Color Fade Protection | Less color retained than 7a; about as much as 11 (cetrimonium cl); brownish | More reddish color retained than 24a, & slightly more than 11, but less than 7 | More red retained than 24b, but still slightly less than 7 | About the same amount of color as 7 | About the same amount of color as 24b; less than 7a. |
| Overall Grade | Fair | Fair | Fair-Good | Good | Fair-Good |

TABLE 4

| INGREDIENT | 31a | 31b | 32a (comparative) | 32b | 33 (comparative) |
|---|---|---|---|---|---|
| GE Silsoft A-843 (25%) | 1% |  | 1% | 1% | 1% |
| Cocotrimonium Chloride (34%) | 2% | 2%. |  | 1% |  |
| Arquad 12-37W (37% active, 95% C12) |  |  |  |  | 2% |
| pH | 6.69 | 8.64 | 5.31 | 5.83 | 5.84 |
| Visual Evaluation of Color Fade Protection | Retained noticeably more reddish color than water soak | Similar to 31a | Slightly less color than 31a/b | Similar to 32a | Very slightly more color retained than 31a/b |
| Overall Grade | Good | Good | Fair-Good | Fair-Good | Good |

The foregoing results show that the monoalkyl quaternary ammonium salts afford color fade protection to dyed tresses. As shown in Table 1, cocotrimonium chloride provides color fade protection, while cationized polysaccharides (Hercules Aquacat liquid guar) and amodimethicone (Clariant Silcare Silicone SEA) do not. Further, the lower alkyl quaternary ammonium salts (i.e., cocotrimonium chloride and laurtrimonium chloride) appear to have greater color fade protective effect, as shown in Tables 2-4. In addition, the length of time that the tresses were dipped in the monoalkyl quaternary ammonium salt solution appears to correlate with greater color fade protection. Tresses soaked for 6, 8, or 10 minutes in the same monoalkyl quaternary ammonium salt solution exhibited greater color retention than tresses soaked for 2 or 4 minutes (see Table 3).

The results also confirm that it is the monoalkyl quaternary ammonium salt that protects the tresses from color fading and that the surfactant in the dipping solutions has no effect on color fading. Tresses treated with a solution containing a monoalkyl quaternary ammonium salt and a surfactant (see, for example, tress no. 7) exhibited good color retention. Tresses treated with a solution containing monoallyl quaternary ammonium salts without a surfactant (see, for example, tress nos. 17 and 31b) exhibited fair-good color retention. In contrast, tresses treated with a solution that contained a surfactant but did not contain a monoalkyl quaternary ammonium salt (see, for example, tress nos. 5 and 20a) exhibited poor color retention and were in fact, similar to controls that were only soaked in water. Therefore, this study demonstrates that monoalkyl quaternary ammonium salts are effective at inhibiting color fade of dyed tresses.

EXAMPLE 2

This example demonstrates the effectiveness of a pre-shampoo treatment in preventing color fade of dyed tresses.

Tresses (5 gm) were dyed with GARNIER 100% Color #660 Intense Auburn or L'OREAL Dark Burgundy Brown 4BR. The tresses were rinsed for 10 seconds and then soaked in 5 ml of one of the monoalkyl quaternary ammonium salt containing pretreatment solutions (A-E) shown in Table 5, for 1, 5, or 10 minutes. Following pretreatment, the tresses were exposed to shampoo (0.6 ml, 1 min.), 15 second rinse, conditioner (1 ml, 2 min.), 15 second rinse, blow-dry, let stand at room temperature for 1 hour. The tresses were subjected to said treatment 5 times. All rinses were with tap water at 35-40° C. The tresses were assessed visually against a control in which there was no pretreatment with one of the monoalkyl quaternary ammonium pretreatment solutions. Regardless of the dye utilized, tresses that were pretreated with a monoalkyl quaternary ammonium pretreatment solution showed greater color intensity following the experiment compared with controls. Further, even tresses soaked in a pretreatment solution for only 1 minute showed greater color intensity compared with controls.

TABLE 5

| INGREDIENT | A | B | C | D | E |
|---|---|---|---|---|---|
| Water | 90.050 | 88.050 | 90.050 | 88.050 | 86.800 |
| Methylparaben | 0.100 | 0.100 | 0.100 | 0.100 | 0.100 |
| Tetrasodium EDTA | 0.100 | 0.100 | 0.100 | 0.100 | 0.100 |
| Hydroxyethyl Cellulose | 0.550 | 0.550 | 0.550 | 0.550 | 0.550 |
| Acetamide MEA | 1.000 | 1.000 | 1.000 | 1.000 | 1.000 |
| Laurtrimonium Chloride (37%)/Arquad 12-W-47 | 6.000 | 10.000 | | | |
| Cocotrimonium Chloride(34%) | | | 6.000 | 10.000 | 10.000 |
| DMDM Hydantoin | 0.2 | 0.2 | 0.2 | 0.2 | 1.05 |
| Imidazolidinyl Urea | | | | | 0.400 |
| Water | 2.000 | | 2.000 | | |
| | 100.000 | 100.000 | 100.000 | 100.000 | 100.000 |

This example demonstrates that pretreatment of tresses prior to color treatment results in greater intensity of color as well as reduced color fade.

Tresses were dipped in a monoalkyl quaternary ammonium salt containing pre-coloring treatment solution shown in Table 6 for 10 min. Tresses were then dyed with CLAIROL Ultress 4RV. Tresses were then soaked overnight in water.

Tresses that were pretreated before dyeing exhibited greater intensity color compared to control tresses that were not pretreated. Further, the pre-color treated tresses visually retained a vibrant color following the overnight soak in water compared to the control tresses, which lost most of their dyed color.

TABLE 6

| INGREDIENT | |
|---|---|
| Water | 97.000 |
| COCOTRIMONIUM CHLORIDE (34%) | 2.000 |
| Bisamino PEG/PPG-41/3 Aminoethyl PG-Propyl Dimethicone (25%) | 1.000 |
| | 100.000 |

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method for enhancing the intensity of color achieved by color-treating human hair comprising:
   contacting the human hair with a composition from about 0.5 minutes to about 30 minutes, wherein said composition comprising water as a carrier and from about 0.25 wt % to about 10.0 wt % of alkyl quaternary ammonium salt in an amount effective to increase the intensity of color in the human hair following color treatment; and
   color-treating the human hair,
wherein, the intensity of color achieved by color-treating the human hair is greater than the intensity of color achieved when the human hair are untreated with the alkyl quaternary ammonium salt;
   wherein said alkyl quaternary ammonium salt is selected from the group consisting of lauryltrimonium chloride, and cocotrimonium chloride.

2. The method of claim 1, wherein the composition further comprises a surfactant.

3. The method of claim 2, wherein the surfactant comprises one or more water-soluble amodimethicones, one or more water-soluble quaternized silicone derivatives, one or more water-soluble nonionic surfactants, one or more water-soluble anionic surfactants, one or more water-soluble amphoteric surfactants, or a combination thereof.

4. The method of claim 2, wherein the surfactant is present in the composition in an amount of from about 0.05 wt % to about 10 wt %.

5. The method of claim 4, wherein the surfactant is present in the composition in an amount of from about 0.1 wt % to about 2.0 wt %.

6. The method of claim 1, wherein the composition further comprises one or more carriers, emulsifiers, one or more thickeners, one or more preservatives, one or more UV protectants, one or more pH adjusting agents, one or more antioxidants, one or more botanical extracts, one or more emollients, one or more fragrances, or a combination thereof.

7. The method of claim 1, comprising contacting the keratinous fibers with the composition for from about 5 minutes to about 10 minutes.

8. The method of claim 1, wherein the composition further comprises DMDM Hydantoin, diazolidinyl urea, or a combination thereof.

9. The method of claim 8, comprising from about 0.1 wt % to about 5.0 wt % DMDM hydantoin.

10. The method of claim 9, comprising about 1.0 wt % DMDM hydantoin.

11. The method of claim 8, comprising from about 0.01 wt % to about 1.0 wt % diazolidinyl urea.

12. The method of claim 11, comprising about 0.4 wt % diazolidinyl urea.

* * * * *